United States Patent [19]

Kostich

[11] Patent Number: 5,782,244
[45] Date of Patent: Jul. 21, 1998

[54] METHOD AND APPARATUS FOR IMMOBILIZING THE HEAD, SHOULDER AND TORSO OF THE HUMAN ANATOMY

[76] Inventor: Jeffrey Vincent Kostich, 7992 Pine Ridge St. NW., North Canton, Ohio 44720

[21] Appl. No.: 598,351

[22] Filed: Feb. 8, 1996

[51] Int. Cl.$^6$ ............................................. A61B 19/00
[52] U.S. Cl. ......................................... 128/869; 128/870
[58] Field of Search ................................ 128/845, 846, 128/869, 870; 5/652, 722, 723, 902; 264/45.2

[56] References Cited

U.S. PATENT DOCUMENTS

| | | | |
|---|---|---|---|
| 2,751,609 | 6/1956 | Oesterling | 5/420 |
| 3,038,175 | 6/1962 | Faget | 5/652 |
| 3,048,169 | 8/1962 | Pierce . | |
| 3,403,676 | 10/1968 | Gibbons . | |
| 4,347,213 | 8/1982 | Rogers, Jr. . | |
| 4,383,713 | 5/1983 | Roston | 5/652 |
| 4,450,122 | 5/1984 | Gallina . | |
| 4,622,185 | 11/1986 | Kostich . | |
| 4,825,487 | 5/1989 | Eberl | 5/652 |
| 4,905,267 | 2/1990 | Miller et al. | 378/208 |
| 5,454,993 | 10/1995 | Kostich . | |
| 5,524,640 | 6/1996 | Lisak | 5/722 |

*Primary Examiner*—Michael A. Brown
*Attorney, Agent, or Firm*—Oldham & Oldham Co., LPA

[57] ABSTRACT

An apparatus for immobilizing and positioning the head, shoulder, and torso region extending down to the mid thigh of the human for radiographic examination or treatment. The device consists of a base board with an extension, a head and shoulder form, a pair of chest side forms and a pair of side rails. A foam mixture is applied to the upper surface of the baseboard and the entire device is placed into a large flexible container or bag. A patient's head, shoulder and torso region are placed on the device in a supine position. The patient remains in a fixed position while the foam mixture expands around the patient's body and the apparatus. After a brief period of time, the foam sets or hardens and a mold or template is formed. This mold serves to immobilize the head, shoulder and torso region extending down to the mid thigh of the body during radiographic examinations and treatment as well as other procedures. The form can be utilized repeatedly with the same patient in subsequent procedure for duplicating the initial examination or treatment posture.

16 Claims, 3 Drawing Sheets

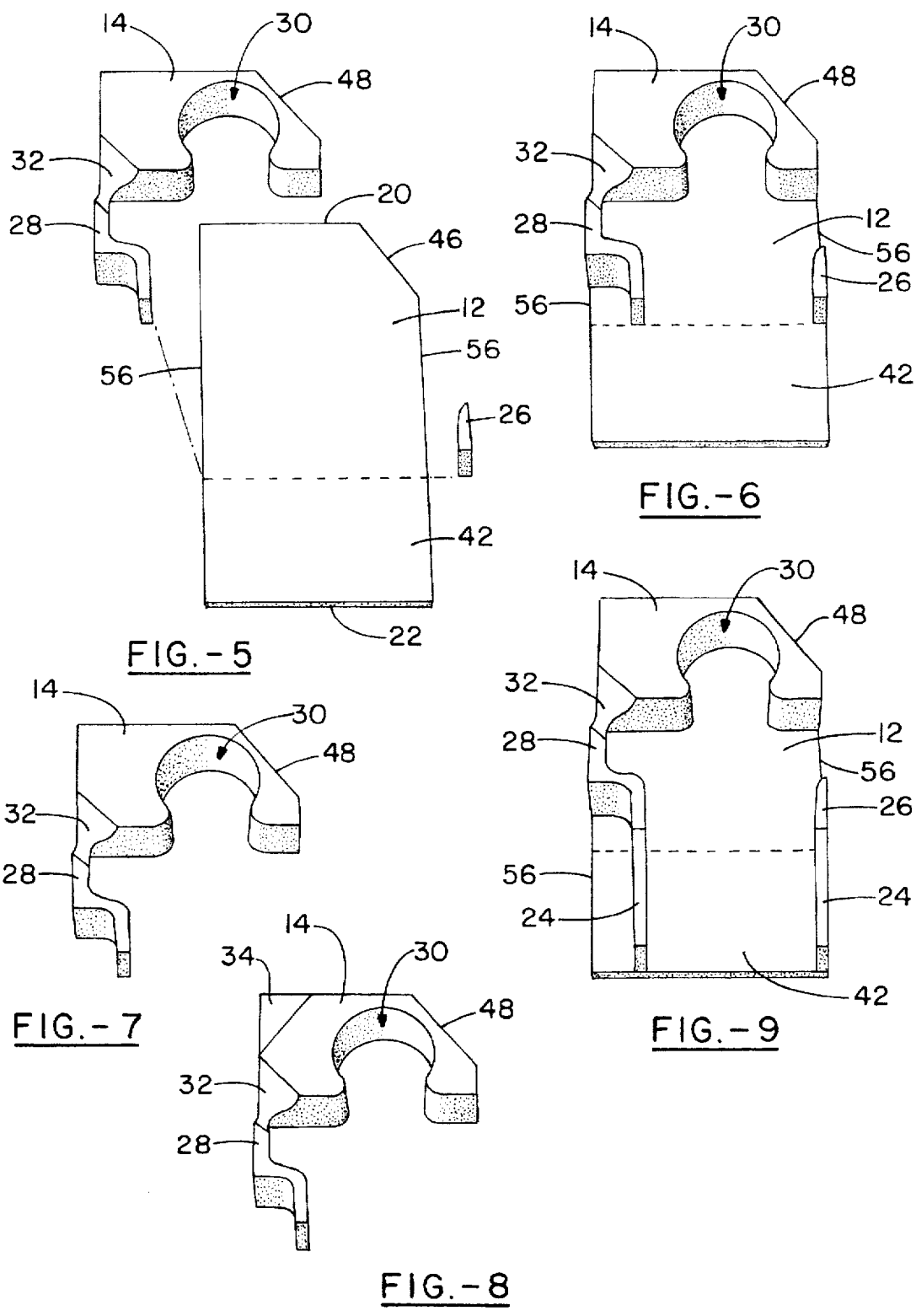

5,782,244

METHOD AND APPARATUS FOR IMMOBILIZING THE HEAD, SHOULDER AND TORSO OF THE HUMAN ANATOMY

TECHNICAL FIELD

This invention relates generally to an apparatus and method for immobilizing a portion of the human anatomy for procedures such as radiographic examinations and treatment. More specifically, the present invention relates to a method and apparatus for developing a mold or template of the head, shoulder and torso extending down to the mid thigh of the human anatomy.

BACKGROUND OF THE INVENTION

The efficiency and effectiveness of certain medical procedures can be considerably enhanced if that portion, or those portions, of the patient's anatomy requiring treatment can be quickly and accurately positioned and comfortably supported during successive treatments. This need to be able to accurately position, and successively reposition, a portion of the patent's anatomy and then maintain it virtually motionless is exemplified by considering a series of radiation treatments. The radiation beam must be projected to an exact location, sometimes interiorly of the body. Such a radiation beam must be most accurate in order not to inflict damage to the tissues surrounding the area to be treated, and as a result there is little margin for error. Not only must the radiation beam be projected accurately toward a particular spot on the body surface, the body must also be precisely oriented to effect the required alignment of the radiation beam from the surface of the body to the interiorly located tissue being treated. Moreover, once the patient is positioned and aligned he/she, must remain as motionless as possible. Radiation treatment generally requires repeated exposures over a period of several weeks. Thus, the difficulties are compounded without a template by which medical personnel can quickly and accurately reposition and support the patient during successive treatments in exactly the same position as initially determined.

Previously, standardized forms have been used which approximate the size of selected portions of the human anatomy. A foam is poured into the form, the patient is positioned within the form, and the foam rises around the contours of the patient and is restricted by the walls of the form. This approach is deficient in that these forms are available in a limited number of standard sizes, typically only pediatric and adult, and, therefore, are not always suitable for a particular patient. Further, the mere size of the standardized forms makes it impractical for a healthcare facility to stock an adequate quantity of numerous sized forms.

Based on these deficiencies, the applicant developed the invention disclosed in U.S. Pat. No. 4,622,185 as a "Method and Apparatus for Molding and Accurately Repositioning Selected Portions of the Human Anatomy", the substance of which is herein incorporated by reference. The device disclosed in that patent consisted essentially of a base containing a plurality of orthogonally disposed grooves or slots. A plurality of slats are provided for removable insertion into the grooves. The slats are cooperatively aligned to substantially encompass the area immediately around that particular portion of the patient's anatomy for which a template is to be formed. A flexible container or bag is placed within the area defined by the slats and a predetermined amount of foam is placed therein. The portion of the patient's body to be molded is placed over the foam filled container and the foam expands around the selected portion of the patient's body. This apparatus and technique is highly versatile and has enjoyed widespread acceptance in the medical community but fails to offer maximum control of lower torso rotation of the human body.

SUMMARY OF THE INVENTION

It is, therefore, a primary object of the present invention to provide an improved method and apparatus for immobilizing portions of the human anatomy and specifically the head, shoulder and torso region.

It is a further object of the present invention to provide an improved method and apparatus for creating an individualized mold for selected portions of the human body and especially the head, shoulder and torso region.

It is still a further object of the present invention to provide an improved method and apparatus for immobilizing and repositioning the head and shoulder portions including the torso down to the mid thigh for complete immobilization of the torso region, hips and internal anatomy of the peritoneal cavity.

These and other objects and advantages are accomplished by an improved method and apparatus which in general comprises a base with an extension, a head and shoulder form, chest side forms, and side rails. A foam mixture is applied to the upper surface of the base and attached forms, and the entire device is placed into a large flexible container or bag. A patient's head, shoulder, and torso region extending down to the mid thigh is placed on the device in a supine position. The patient remains in a fixed position while the foam mixture expands around the patient's body and the apparatus framework. After a brief period of time, the foam sets or hardens and a mold or template is formed.

In this manner, a mold or template is created which can be used to immobilize the head, shoulder and torso region of the human body during certain medical procedures including X-rays, CAT-scans, MRI and other radiographics procedures and therapeutic treatment of patients using external radiation. The template is reused in similar subsequent procedures for placing that portion of the human body in the same position that it was in during the initial procedure, resulting in an increased ability for medical personnel to isolate, examine or treat a target area of the patient's body.

BRIEF DESCRIPTION OF THE DRAWINGS

FIG. 5 is an assembly drawing illustrating the various parts of the apparatus for creating a template of the head, shoulder and torso region extending down to the mid thigh of the human anatomy used for treating breast conditions.

FIG. 6 is a perspective view of the apparatus shown in FIG. 5.

FIG. 7 is a perspective view of one embodiment of the head and shoulder form without an arm rest.

FIG. 8 is a perspective view of one embodiment of the head and shoulder form with an arm rest.

FIG. 9 is a perspective view of the apparatus shown in FIG. 5 with the addition of sider rails for the inferior or lower portion of the human anatomy.

DETAILED DESCRIPTION OF THE PREFERRED EMBODIMENT

Figure 1:
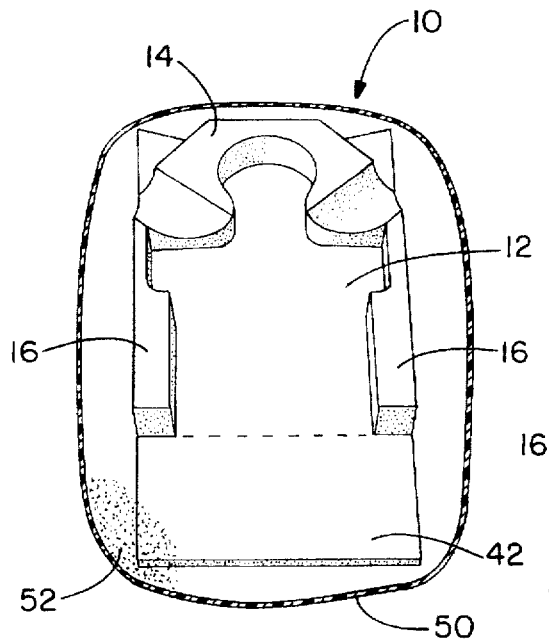
FIG. 1 is a perspective view of the apparatus for creating a template of the head, shoulder and torso region extending down to the mid thigh of the human anatomy according to the present invention.

Now with reference to the invention illustrated in the drawings and specifically FIG. 1, an apparatus for creating a mold or template for the head, shoulder and torso region extending down to the mid thigh of the human body is shown generally by numeral 10. The template forming apparatus consists generally of an essentially planar base 12 with an extension 42, a head and shoulder form 14, a pair of chest side forms 16, a pair of side rails 24 (shown in FIG. 3), a flexible bag or container 50, and a foaming mixture 52.

Figure 2:
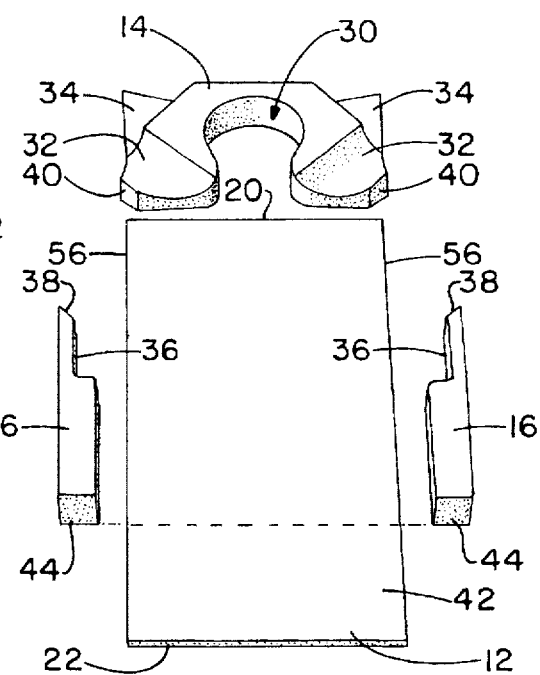
FIG. 2 is an assembly drawing illustrating the various parts of the apparatus shown in FIG. 1.

Base 12, as shown in FIG. 2, is essentially rectangular in shape and has an upper surface 18, although it is appreciated that a variety of alternative shapes are possible. In the preferred embodiment planar base 12 is composed of an extruded polystyrene material sufficient to support the weight of a patient for which the mold is being created. Numerous other materials would be recognized as suitable by those of ordinary skill in the art.

In FIG. 2, a head and shoulder form 14, preferably made from an expanded polystyrene material and having a width substantially equal to the width of base 12, is attached to the upper surface 18 of planar base 12 at or near its top 20. Head and shoulder form 14 is attached to base 12 by means known in the art but preferably contact adhesive or double-sided tape products. Head and shoulder form 14 may be fabricated from several pieces of polystyrene but in the preferred embodiment is fabricated from a single piece. A substantially rectangular block of polystyrene material with the appropriate forms cut out comprises head and shoulder form 14. In one embodiment of head and shoulder form 14, a head cavity 30 generally shaped as a human head when positioned in the supine position is created by removing a section of polystyrene from the substantially rectangular block of polystyrene. Additionally, symmetrical arm channel regions 32 are formed in head and shoulder form 14 which allow a patient to place his arms above his head comfortably. Depending on the goals of the therapy, different head and shoulder forms 14 can be used which have arm channel regions 32 formed for different arm positions and elevations. For further patient comfort, symmetrical arm rests 34 are formed in head and shoulder form 14 at a tangential angle to that of arm channel regions 32. When a patient is required to maintain his arms above his head the natural reaction is to bend ones arms thereby forming a V shape from each elbow. Without arm channel regions 32 and arm rests 34, patients would experience discomfort when trying to maintain a steady position under their own strength. The most important considerations for proper patient positioning is the safety and comfort of the patient. Head and shoulder form 14 serves as a support which cradles the patient in the desired set-up position. By increasing the level of comfort for the patient, the patient is less likely to move during treatment.

Several other contemplated embodiments of head and shoulder form 14 are shown in FIGS. 5 through 9. Referring now to FIGS. 5 and 6, head and shoulder form 14 is constructed and attached to planar base 12 in the same manner as described earlier for FIGS. 1 through 4. This alternative embodiment of head and shoulder form 14 is designed for treating patients undergoing any number of types of breast therapy. Head and shoulder form 14 has a head cavity 30 with one arm channel region 32 which then extends away from head cavity 30 to form an integral chest side form 28. Head cavity 30, arm channel region 32, and integral chest side form 28 are only formed on whichever side the breast to be treated is located. Depending on the needs of the patient, head and shoulder form 14 may be equipped with an arm rest 34 as shown in FIG. 8 or without one as shown in FIG. 7. For breast therapy, the top 20 of planar base 12 has an angled corner 46 and head and shoulder form 14 has an angled corner 48. The two angled corners, 46 and 48 respectively, compliment one another and provide a simple means of alignment when head and shoulder form 14 is attached to planar base 12. The angled corners 46 and 48 are located on the side opposite the side of the breast to be treated, that being the same side that arm channel region 32 and integral chest side form 28 are located. This modification to the preferred embodiment allows immobilized patients to fit through the tunnel of most treatment equipment. It is to be understood that many different variations of head and shoulder form 14 are contemplated by the applicant and the specific shapes and configurations described are not to limit the scope of the claimed invention.

Referring back to FIG. 2, a pair of chest side forms 16 are attached to upper surface 18 of planar base 12 by means similar to those used to attach head and shoulder form 14, preferably by means of adhesive. Chest side forms 16 are substantially elongated rectangular blocks with shoulder relief cutouts 36 on one side. Shoulder relief cutout 36 begins at the top 38 of each chest side form 16 and ends at a predetermined distance which in the preferred embodiment is less than half the length of chest side form 16. The length and size of shoulder relief cutouts 36 are different for different patients and as such the inventor contemplates variations such as shoulder relief cutouts 36 which are approximately the full length of the chest side forms 16. Because there are many variations depending on the patient, the treatment, and the physician, the invention is not to be limited by the specific configuration described.

Chest side forms 16 are attached to the upper surface 18 and along the sides 56 of planar base 12 so that the tops 38 of shoulder relief cutouts 36 are abutted with angled edges 40 of head and shoulder form 14. The tops 38 of shoulder relief cutouts 36 are angled complimentary to angled edges 40 of head and shoulder form 14 in order to provide for proper mating and positioning when chest side forms 16 are attached to planar base 12. The angled edges make proper alignment during production easier as there is only one position that will fit correctly which ensures that shoulder relief cutouts 36 are always located along the sides 56 and facing towards the center of planar base 12. Less time and supervision is necessary while maintaining correct and quality production of template forming or patient repositioning apparatus 10.

FIG. 6 shows an alternate embodiment of apparatus 10 with different side forms used for breast therapy. Head and shoulder form 14 comprises integral chest side form 28 extending from arm channel region 32. Chest side form 28 could be a separate component but it is preferred that it be integral with head and shoulder form 14 for easier assembly and consistent positioning accuracy. To immobilize the patient properly, a short chest side form 26 is attached through known means to planar base 12 on the opposite side of and parallel with integral chest side form 28.

Figure 3:
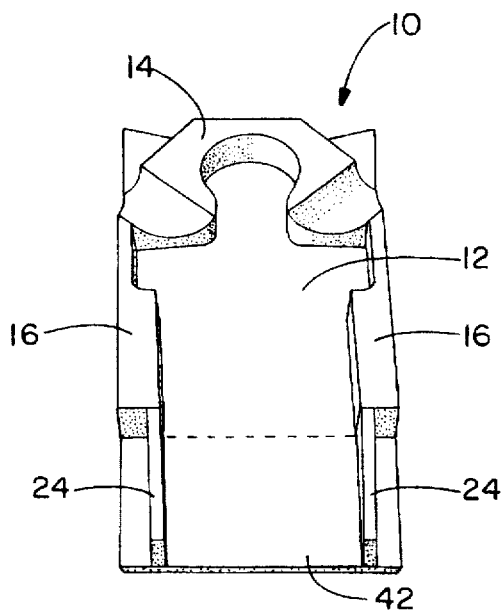
FIG. 3 is a perspective view of the apparatus shown in FIG. 1 with the addition of side rails for the inferior or lower portion of the human anatomy.
Figure 4:
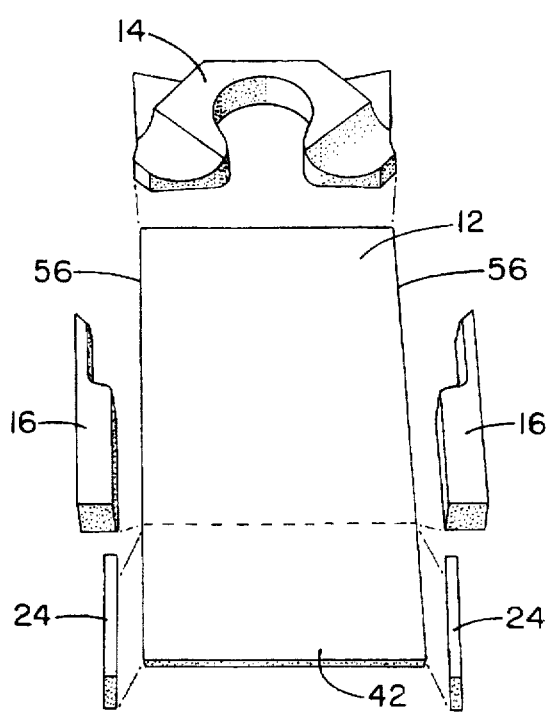
FIG. 4 is an assembly drawing illustrating the various parts of the apparatus shown in FIG. 3.

Patient repositioning systems have been used in medical treatment for several years and while providing satisfactory results the present invention has an advantage by providing improved control of torso rotation through apparatus 10's extended base 42 as shown in FIGS. 1 through 6 and 9. Referring to FIG. 2, extended base 42 is the region of planar base 12 that extends past the bottoms 44 of chest side forms 16. In the preferred embodiment the total length of planar base 12 is approximately five feet and may vary depending upon the patient and the specific treatment prescribed. Earlier immobilization forms without extended base 42 caused difficulties in patient set up. By extending planar base 12 caudally to the mid thigh, extended base 42 immobilizes the patients pelvis and thighs when the template forming apparatus 10 is molded to the individual patient. Extended and planar base 12 provides complete immobilization of the torso region, hips and internal anatomy of the peritoneal cavity of a patient. FIG. 3 shows side rails 24 which are attached to planar base 12 in the same manner as other components previously described and are aligned so as to act as extensions of and from the bottom 44 of chest side forms 16. Side rails 24 act as retaining walls which force foaming mixture 52 in toward the patient's torso.

In a study done for applicant to assess the effect of extended base 42, the number of patient misalignments observed on port films was compared with that of the same number of patients treated using a template forming or immobilization form without an extended base. Review of the port films revealed that the misalignment rate for the form without an extended base was greater than the test group which had the extended base. In addition the tests also showed that the size of the misalignment errors was larger in the test group which did not have the extended bases. FIG. 9 shows an alternative embodiment of apparatus 10 used for breast therapy having extended base 42 and side rails 24. Similar testing of this embodiment lead to the same results, that being improved misalignment rates and much more aggressive patient immobilization.

The extended base apparatus not only performed better but the technologists who performed the tests reported that they could set up treatments faster when patients are positioned in a body mold which is the result of having extended base 42 and side rails 24 for inferior or lower portions of the human body. The extended base 42 and side rails 24 reduced the number of repeat port films which also saves time, both in terms of taking and developing the films, and it also reduces the physicians' time because there are less port films to review. Other savings are recognized in terms of amount of films needed and in space required for film storage. The most important gain however, lies with the fact that the patients feel comfortable, relaxed and are secure on what are normally narrow treatment couches.

Once the head and shoulder form 14, chest side forms 16, and side rails 24 are positioned and attached on the upper surface 18 of planar base 12, a foam mixture 52 is applied to apparatus 10.

Foam mixtures that are suitable for practice of the present invention are not in themselves particularly unique and may include the polyurethane family. Various formulations of the polyurethane family are employed to provide foams having widely disparate, ultimate characteristics. For example, some formulations provide foam that is hydrophilic and are, therefore, eminently suited to be used for supports for floral displays. Other formulations provide foam that possesses antipodal characteristics, and which are, therefore, eminently suited to be used in, or as, flotation devices.

In order to be suitable for use in medical applications, such as the present, foam compositions must exhibit a low foaming temperature so as not to create a potential of causing a burn to the patient. Further, it is desirable that any foam composition have a quick hardening time and have sufficient integrity to immobilize the particular body portion as well as support the necessary weight of the patient. One specific formulation which is well suited to this method and apparatus is the polyurethane foam composition set out in U.S. Pat. No. 4,771,082. This polyurethane foam composition has a maximum foaming temperature of 45 degrees Celsius and hardens in approximately 8–10 minutes.

The basic reaction is that of mixing a polyol and a polyisocyanate such as follows:

$$\underset{\text{diol}}{\text{HO}-\text{R}-\text{OH}} + \underset{\text{diisocyanate}}{\text{O}=\text{C}=\text{N}-\text{R}-\text{N}=\text{C}=\text{O}}$$

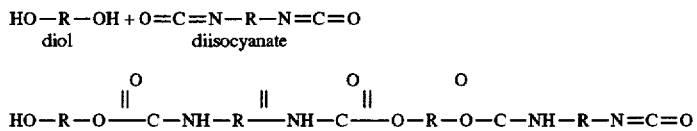

Surfactants, catalysts and blowing agents are generally added in various amounts selectively to provide the desired properties from the wide range available, including such characteristics as hydrophilia rate of rise, rate of cure, amount of heat release, cell size and rigidity. The preferred polyisocyanate for practice of the subject invention is polymethylenepolyvinyl isocyanate, whereas the preferred polyol is a mixture of various polyols such as ethylene glycol, glycerin 2,2 dimethyl-1,3-butanediol, 1,2,4 butanetriol, 1,2,6 hexanetriol and the like.

A typical application of the present invention to mold a template for any selected portion of a patient's anatomy would employ the addition of approximately 100 ml to 350 ml of the polyol to 75 ml to 240 ml of the polyisocyanate.

The chemicals required to form the foam are then mixed together. Typically the polyisocyanate is provided in a bottle larger than that required, and the bottle in which the polyol is provided is emptied into the bottle containing the polyisocyanate. The bottle now contains the mixed polyisocyanate and polyol is then capped and vigorously shaken for approximately 35 seconds. Thereafter, the bottle is opened and the contents are poured onto base 12. The foam mixture 52 is spread as evenly as possible over the base.

A barrier means is then placed over the entire upper surface 18 of the foam-containing apparatus 10. The barrier means is illustrated in FIG. 1 as a flexible container or bag 50 with the entire apparatus 10 contained therein. Ideally, air is allowed to circulate inside the bag until bubbles are noted in the foam (1–3 minutes). The air is then forced out, the bag is sealed and the patient is placed in the foam. However, a sheeted material placed over the entire upper surface of apparatus 10 and insulating the patient from any contact with the foam mixture can be used. The barrier means must be tear-resistant, flexible and must not react with the selected foam mixture. A suitable barrier means may be fabricated from a pliable, sturdy material such as polyvinyl-chloride (PVC).

Even though PVC has proven to be a perfectly acceptable material, it should be appreciated that the wall thickness of the bag should be no less than approximately 1.5 mils. Hence, some standard refuse bags, even though made of PVC, cannot be used because their wall thickness if too thin. Some industrial refuse bags, and certain brands of those home refuse bags advertised as having "double wall" thickness, or the like, as well as certain brands of waste compactor bags, however, do possess the requisite wall thickness, and they may be employed.

This minimal wall thickness is required to accomplish two objectives. First, a wall thickness of less than 1.5 mils is too subject to tearing or rupturing. The flexible container 50 must provide a controlled confinement for the foam mix, if the invention is to be satisfactorily employed, and the objective cannot be achieved if the flexible container 50 ruptures, or tears. Second, a wall thickness of less than 1.5 mils is too susceptible to wrinkling and could cause an undesirable fold where it might not be visually detectable. Such unobserved folds can capture the foam mixture before it fully foams to create localized "hot spots" that could make the patient uncomfortable, at the least, or, at the worst, burn the patient. Such localized hot spots have been observed to melt the PVC bag at, and around, such a fold. Employing a PVC bag having sufficient wall thickness, however, has been found to obviate this potential problem.

A flattened bag measuring approximately 54×246 inches (137.2 by 61 cm) provides a convenient size that can be readily adapted to virtually any situation, as will become apparent from the hereinafter described exemplary usage.

It is to be understood that the foam mixture 52 can be applied to apparatus 10 as previously explained, after the apparatus has been placed with a flexible container or bag 50.

Figure 10:
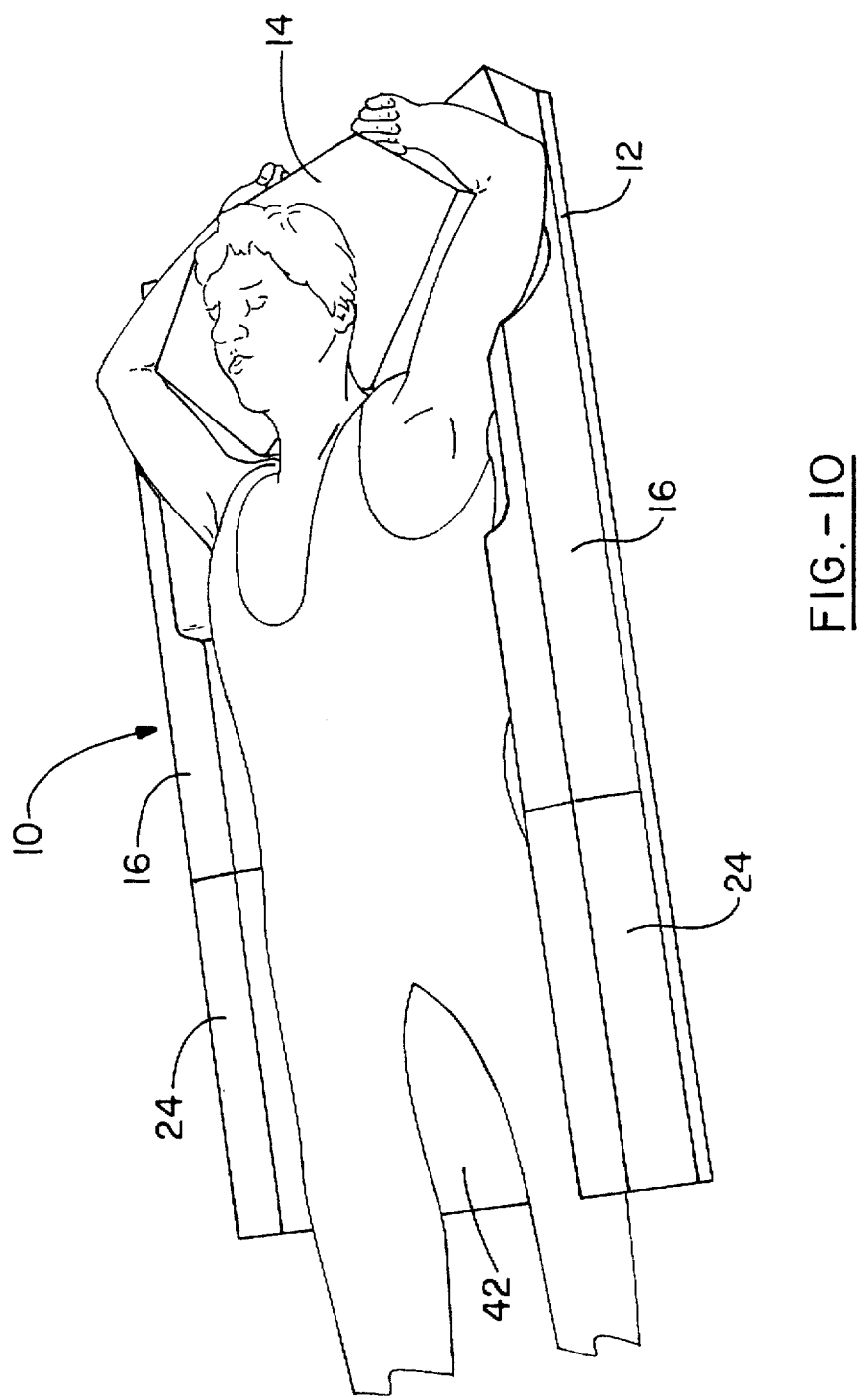
FIG. 10 is a perspective view of a patient's body placed into contact with the template forming apparatus of the claimed invention.

After the foam has been applied to the upper surface 18 of base 12 and the barrier means applied, that portion of the patient's body for which the template or mold is to be made is placed into contact with the apparatus 10 as shown in FIG. 10. As the foam begins to expand and rise, it begins to pull a portion of the barrier means 50 away from apparatus 10 and into conforming contact with the patient's body portion. As the patient remains in a stable non-moving state, the foam hardens to form an impression of the particular body part. The foaming action typically subsides after about fifteen minutes, and thereafter, the patient can be carefully extricated from the newly formed mold. The mold should then be permitted to harden for a period of five to thirty minutes.

Therefore, upon reinsertion into the mold the particular portion of the patient's body to be examined will be returned or repositioned just as it was at the time of mold formation. The resulting apparatus or mold can be used in successive procedures involving the same portion of the body to consistently duplicate the previous positioning and immobilization. The template made in accordance with this invention can also be further modified for the type of treatment desired, for example, by cutting access holes directly through the template.

In the preferred embodiment of the present invention, planar base 12, side rails 24, head and shoulder form 14, and chest side forms 16 are made from extruded or expanded polystyrene materials because of the material's light weight, durability for this intended purpose and affordability. Even more importantly, polystyrene products are substantially radiolucent. In this way, transmission of irradiation treatment can take place through the apparatus and/or hardened foam with minimal, if any, interference or distortion. However, numerous other material could be used to accomplish the purposes of this invention. The elements of the present invention can be supplied in the form of a single kit for use with patients of varying size.

It should be apparent that the invention accomplishes the objects thereof. As stated, a variety of boards, supports, spacers, foam mixtures and methods of attaching to the base can be employed in the practice of this invention. It is to be understood that such variations are intended to fall within the scope of the claimed invention and that the subject invention is not to be limited by the specific method of operation described and/or depicted by the drawings nor is the invention to be limited by the specific chemical and mechanical components identified and described herein. There have been designated merely to provide a demonstration of operability and the selection of mechanically equivalent arrangements is not deemed a departure from the spirit of the invention being limited solely by the scope of the attached claims.

What is claimed is:

1. A method of forming a mold for immobilizing the head, shoulder and torso region extending down to the mid thigh of the human anatomy comprising the steps of:
    a) providing a foamed template structure;
    b) applying a foam mixture to the area of said foamed template structure;
    c) placing a barrier means over said foamed template structure;
    d) positioning said head, shoulder and torso region extending down to the mid thigh of the human anatomy onto said foamed template structure in a supine position; and
    e) maintaining said head, shoulder and torso region extending down to the mid thigh of the human anatomy in a fixed position for a sufficient length of time for said foam mixture to set and form a mold therefore.

2. The method of forming a mold as recited in claim 1 wherein said foamed template structure comprises a planar base, a head and shoulder form attached to the upper surface of and at the top of said planar base, and at least one chest side form attached to said upper surface of said planar base along the side of said planar base.

3. The method of forming a mold as recited in claim 2 wherein said head and shoulder form comprises a rectangular block, said rectangular block having a cavity for receiving a human head, and at least one channel for receiving part of a human arm.

4. The method of forming a mold as recited in claim 3 wherein said head and shoulder form further comprises an arm rest formed in said rectangular block for receiving part of a human arm.

5. The method of forming a mold as recited in claim 2 wherein said planar base extends beyond the bottom of said at least one chest side form.

6. The method of forming a mold as recited in claim 2 comprising the further step of attaching at least one side rail to the upper surface of and along the side of said planar base, said at least one side rail abutted to and extending from the bottom of said at least one chest side form.

7. The method of forming a mold as recited in claim 2 wherein said head and shoulder form comprises a rectangular block, said rectangular block having a cavity for receiving a human head, at least one integral channel for receiving part of a human arm, and at least one integral chest side form.

8. The method of forming a mold as recited in claim 2 wherein said foamed template structure further comprises at least one side rail attached to the upper surface of and along the side of said planar base, said at least one side rail abutted to and extending from the bottom of said at least one chest side form.

9. The method of forming a mold as recited in claim 1 wherein said barrier means comprise a flexible container.

10. The method of forming a mold as recited in claim 1 comprising the further steps, inserted between steps (c) and (d), of:

allowing air to circulate inside of said flexible container for a length of time; and expelling said air from said bag and sealing said bag.

11. The method of forming a mold as recited in claim 1, wherein said foam mixture is produced by mixing the contents of a first container means containing a polyol mixture to the contents of a second container means containing polyisocyanate.

12. The method of forming a mold as recited in claim 11, wherein the ratio of said polyol mixture to said polyisocyanate ranges from about 1:3 to about 5:1.

13. A method of forming a mold for immobilizing the head, shoulder and torso region extending down to the mid thigh of the human anatomy comprising the steps of:

a) providing a foamed template structure;

b) placing a barrier means over said foamed template structure;

c) applying a foam mixture to the area of said foamed template structure;

d) positioning said head, shoulder and torso region extending down to the mid thigh of the human anatomy onto said foamed template structure in a supine position; and e) maintaining said head, shoulder and torso region extending down to the mid thigh of the human anatomy in a fixed position for a sufficient length of time for said foam mixture to set and form a mold therefore.

14. A device for forming a mold for immobilizing the head, shoulder and torso extending down to the mid thigh of the human anatomy comprising;

a base for supporting a molded template structure, said base having upper and lower planar surfaces, a top, a bottom and at least two sides;

a head and shoulder form attached to the top and upper surface of said base, said head and shoulder form having a cavity for receiving a human head, and at least one channel for receiving part of a human arm; and at least one chest side form, having a top and a bottom, attached to said upper surface of said base along at least one of said two sides and adjacent said head and shoulder form, wherein said base extends beyond the bottom of said at least one chest side form.

15. The device as recited in claim 14 further comprising a flexible container means for receiving said base, said head and shoulder form and said at least one chest side form therein.

16. The device as recited in claim 15 further comprising a foam mixture applied to said base, said head and shoulder form and said at least one chest side form, and which after said head, shoulder and torso region extending down to the mid thigh is positioned in said device and a length of time passes, said foam sets to form a mold.

* * * * *